United States Patent
Hofer et al.

(10) Patent No.: US 7,157,449 B2
(45) Date of Patent: Jan. 2, 2007

(54) MEDICAMENT FOR THE TREATMENT OF DISEASES CAUSED BY PARASITIC PROTOZOA

(76) Inventors: Anders Hofer, Kassjö 445, S-905 93 Umeå (SE); Lars Thelander, Torparvägen 14, S-913 42 Obbola (SE)

( * ) Notice: Subject to any disclaimer, the term of this patent is extended or adjusted under 35 U.S.C. 154(b) by 317 days.

(21) Appl. No.: 10/258,810

(22) PCT Filed: Apr. 20, 2001

(86) PCT No.: PCT/SE01/00864

§ 371 (c)(1),
(2), (4) Date: Oct. 28, 2002

(87) PCT Pub. No.: WO01/80809

PCT Pub. Date: Nov. 1, 2001

(65) Prior Publication Data

US 2003/0109505 A1    Jun. 12, 2003

(30) Foreign Application Priority Data

Apr. 27, 2000  (SE) ................................... 0001531

(51) Int. Cl.
A61K 31/655 (2006.01)
A61K 31/519 (2006.01)
A61K 31/522 (2006.01)
A61K 31/7076 (2006.01)

(52) U.S. Cl. ........................ 514/150; 514/45; 514/47; 514/46; 514/48; 514/263.4; 514/263.37; 514/895; 514/262.1; 536/25.32; 536/22.1; 536/25.31; 536/23.1; 562/573; 435/69.1

(58) Field of Classification Search ................ 514/150, 514/45, 46, 47, 48, 50, 263.4, 263.37, 262.1, 514/895; 562/573; 536/25.32, 22.1, 25.31, 536/26.6, 26.71, 27.6, 28.4, 23.1; 544/277; 435/69.1

See application file for complete search history.

(56) References Cited

U.S. PATENT DOCUMENTS 5,180,714 A * 1/1993 Sufrin et al. .................. 514/46

(Continued)

FOREIGN PATENT DOCUMENTS

WO    98/31375    7/1998

OTHER PUBLICATIONS

Queen et al. "In vitro susceptibilities of Plasmodium falciparum to compounds which inhibit nucleotide metabolism." Antimicrob Agents and Chemotherapy, Jul. 1990, 34(7), pp. 1393-1398.*

(Continued)

Primary Examiner—Shaojia Anna Jiang
Assistant Examiner—Devesh Khare
(74) Attorney, Agent, or Firm—Buchanan Ingersoll & Rooney PC

(57) ABSTRACT

The present invention relates to the use of an inhibitor of CTP synthetase, such as a glutamine analogue, and a substance capable of suppressing toxic effects thereof in vivo, in the manufacture of a medicament for the treatment of a disease caused by a parasitic protozoa. More specifically, said substance capable of suppressing toxic effects may be a nucleobase, such as a purine base or a nucleoside, while the glutamine analogue advantageously is 6-diazo-5-oxo-L-norleucine (DON). The invention also relates to a pharmaceutical composition as such for the treatment and/or prevention of a disease caused by a parasitic protozoa, wherein the disease is selected from the group consisting of malaria, leishmaniasis and trypanosomiasis, e.g. American trypanosomiasis (Chaga's disease), or African trypanosomiasis (African sleeping sickness).

10 Claims, 6 Drawing Sheets

U.S. PATENT DOCUMENTS 5,776,718 A * 7/1998 Palmer et al. .............. 435/23
6,159,953 A * 12/2000 Rathod .................... 514/49
6,242,428 B1 * 6/2001 Weis et al. ................ 514/44

OTHER PUBLICATIONS

Mukherjee et al. "Acivicn: A highly active potential chemotherapeutic agent against visceral leishmaniasis." Biochemical and Biophysical Research Communications, vol. 170, No. 2, pp. 426-432, 1990.*

Tanmoy Mukherjee et al, "Acivicin: A Highly Active Potential Chemotherapeutic Agent Against Visceral Leishmaniasis," Biochemical and Biophysical Research Communications, vol. 170, No. 2, pp. 426-432, 1990.

Takashi Aoki et al, "Quantitative Determination of Trypanosoma Cruzi Growth inside Host Cells In Vitro and Effect of Allopurinol," Purine and Pyrimidine Metabolism in Man VIII, pp. 499-502, 1994.

Kenneth E. Kinnamon et al, "Activity of Anticancer Compounds Against Trypanosoma Cruzi-Infected Mice," Am. J. Trop. Med. Hyg., vol. 58, No. 6, pp. 804-806, 1998.

Kim E. Nichols et al, "Monocytoid Differentiation of Freshly Isolated Human Myeloid Leukemia Cells and HL-60 Cells Induced by the Glutamine Antagonist Acivicin," Blood, vol. 74, No. 5, pp. 1728-1737, 1989.

* cited by examiner

MEDICAMENT FOR THE TREATMENT OF DISEASES CAUSED BY PARASITIC PROTOZOA

TECHNICAL FIELD

The present invention relates to the manufacture of a medicament for the treatment of a disease caused by a parasitic protozoa and to a pharmaceutical composition as such.

BACKGROUND

Like virus, bacteria, fungi and algae, protozoa is distinct from higher organisms in that they lack the specialized organization of the cells of higher order living systems. Protozoa, which occur in the kingdom Protista, is a microbial species sometimes denoted a predator, since it derives its nutrition from ingestion of bacteria. Many widespread diseases are caused by protozoan pathogens, such as malaria, leishmaniasis and trypanosomiasis. The last mentioned is caused by infections with species of the protozoan genus *Trypanosoma*. American trypanosomiasis, or Chaga's disease, is caused by *T. cruzi*, which is usually transmitted to humans by infected triatomid bugs, while African trypanosomiasis, or African sleeping sickness, is caused by infections of *Trypanosoma brucei rhodiense* and *T. b. gambiense*. More specifically, African sleeping sickness (for a review see Brun, R. (1999) *Karger-Gazette* 63, 5–7) is a devastating disease that has got its name from the comatose condition at the final stage of the disease. Without treatment, the patient dies within a couple of months to several years after infection. The severe comatose condition described occurs when these parasites from mainly being circulating in the bloodstream also invade the central nervous system.

*T. brucei* is spread between its mammalian hosts by tsetse flies. The parasite goes through many different life cycle stages in the mammalian host as well as in the fly (Vickerman, 1985). When the trypanosomes enter the mammalian host through a tsetse bite, they start to proliferate as long slender bloodstream forms. While the disease progresses, more and more trypanosomes are converted to short stumpy forms that are unable to proliferate but in contrast to the long slender forms can be transmitted to a new tsetse fly. In the fly, the trypanosomes go through some further developmental stages before they are passed on to a new mammalian host.

Most drugs effective against *T. brucei* do not cross the blood-brain barrier and are therefore useless as soon as the trypanosomes have invaded the CNS. Currently, the only drugs effective against a late stage *T. brucei* infection are difluoromethylornithine (DFMO) and arsenicals such as Melarsoprol. The arsenicals have severe side effects and the patient often dies from a drug-induced encephalitis. DFMO is less toxic but very expensive to make and is only effective against *T. b. gambiense*. Due to economic reasons, it is not produced anymore.

In order to find alternative treatments, purine metabolism has for a long time been a hot subject in the field of trypanosomes and related organisms (reviewed in Hassan, H. F. and Coombs, G. H. (1988) *FEMS Microbiol. Rev.* 54, 47–84). It has previously been established that trypanosomes lack the ability to form purines de novo and therefore need hypoxanthine, adenine or guanine which are salvaged through various phosphoribosyltransferases. Any of these three bases is fine since the trypanosomes, like most organisms, have all the enzymes needed to interconvert IMP, AMP and GMP. Nucleosides (adenosine, inosine and guanosine) can also be used, but they are usually split into sugar and base before their salvage (Pellé, R., Vern, L. S., Parkin, D. W. (1998) *J. Biol. Chem.* 273, 2118–2126 *Proc. Am. Ass. Cancer Res.* 22, 352).

However, much less attention has been focused on the synthesis of pyrimidines in trypanosomes (for a review see Hassan, H. F. and Coombs, G. H. (1988) *FEMS Microbiol. Rev.* 54, 47–84). It is known that *T. brucei* is fully capable of making UTP de novo and by salvage of uracil. Since there is no information whether *T. brucei* synthesizes CTP de novo or by salvage of cytidine or cytosine, up to now, it has not been possible to develop drugs based on the control of CTP levels.

SUMMARY OF THE PRESENT INVENTION

According to the present invention, it has for the first time been shown that unlike mammalian cells, the trypanosomes do not have any salvage pathway for CTP synthesis. Instead, CTP is only synthesized de novo. Thus, the invention relates to the use of a CTP synthetase inhibitor in the manufacture of a medicament for the treatment of a disease caused by any parasitic protozoa wherein CTP is synthesized de novo by CTP synthetase. Preferably, a CTP synthetase inhibitor in the form a glutamine analogue is used, in which case a further component may be used to suppress toxic effects thereof that may harm the patient who is given the medicament. Accordingly, the present invention provides for the first time a non-toxic and cost-effective medicament.

DETAILED DESCRIPTION OF THE INVENTION

Figure 1:
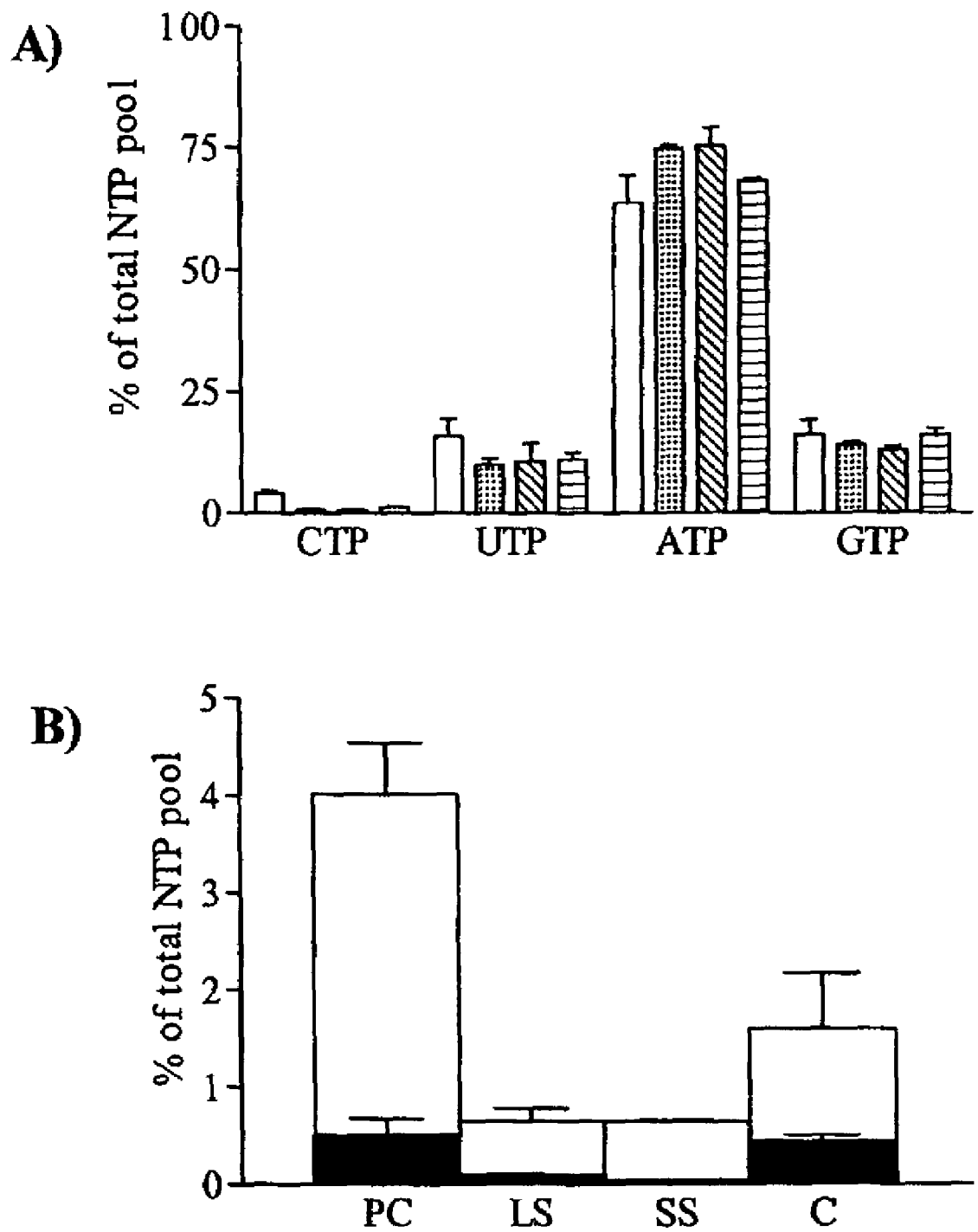
FIG. 1 shows NTP pools in *T. brucei* from different life cycle stages. In A), all the NTPs are shown while in B), the region showing the CTP pools have been magnified. The samples are from procyclic (PC), long slender (LS), short stumpy (SS) and in vitro cultured blood stream forms (C). The abbreviation for each life cycle stage (PC, LS, SS, C) is put below the corresponding box in B) and the same order of the samples are used in A). The values are represented as relative (in %) to the total NTP pool (CTP+UTP+ATP+GTP).

In a first aspect, the present invention relates to the use of an inhibitor of CTP synthetase, especially a glutamine analogue, in combination with a further substance, such as a nucleobase, capable of alleviating toxic effects of said glutamine analogue, in the manufacture of a medicament for the treatment of a disease caused by a parasitic protozoa. More specifically, said nucleobase can be one of the known nucleosides or purine bases or any derivative or functional analogue thereof, as long as it is capable of inhibiting, or at least essentially suppressing, toxic effects of the glutamine analogue when the medicament is administered to a patient. As will appear below, the main role of the glutamine analogue is considered to be inhibiting certain steps in nucleotide biosynthesis.

As mentioned above, the present invention is based on the finding that unlike mammalian cells, the trypanosomes do not have any salvage pathway for CTP synthesis. Instead, CTP is synthesized de novo. Mammalian cells are known to be more versatile when it comes to nucleotide metabolism and they are capable of making purine bases as well as pyrimidines de novo. The salvage pathways include phosphoribosyltransferases (for adenine, hypoxanthine, guanine and uracil) as well as ribonucleoside kinases (for adenosine, guanosine, uridine and cytidine). CTP can both be obtained by salvage of cytidine and by de novo biosynthesis from UTP. The latter reaction is catalyzed by CTP synthetase.

Further, the present inventors have previously reported (Hofer, A., Ekanem, J. T. and Thelander, L. (1998) *J. Biol. Chem.* 273, 34098–34104) that cultured bloodstream *T. brucei* have an exceptionally small CTP pool compared to the other NTP pools and to other types of cells. In the present work, the two stages in the mammalian host and the procyclic form were studied, which is the first of three stages in the fly. The other insect forms can only be obtained by dissecting tsetse-flies.

Thus, according to the present invention, it has now been confirmed that *T. brucei* also have an exceptionally small CTP pool in long slender and short stumpy trypanosomes grown in mice. It is also shown herein for the first time that CTP can only be formed de novo and that it is a slow synthesis rather than an excessive degradation that is responsible for the low CTP level. All these observations have led the inventors towards CTP synthetase as an interesting target for chemotherapy. Further, in the context of *Plasmodium falciparum*, it has been shown to lack cytidine uptake and de novo purine synthesis, see Hassan-HF and Coombs_GH (1988): Purine and pyrimidine metabolism in parasitic protozoa. FEMS Microbiology Reviews 54, 47–84.

As mentioned above, the inhibitor of CTP synthetase is any functional analogue, derivative, substitution product, isomer, or homologue of the amino acid glutamine, which retain the property of glutamine to bind CTP syntetase. Thus, the term "glutamine analogue" is intended herein to encompass any one of the above mentioned. The preparation of glutamine analogues according to the invention are prepared by conventional methods well known to the skilled in this field, see for example the references mentioned below in the context of specific embodiments, or standard reference literature.

In a particularly advantageous embodiment, the inhibitor of CTP synthetase is a norleucine derivative, such as 6-diazo-5-oxo-L-norleucine (DON). DON is a glutamine analogue that inhibits a wide range of glutamine requiring reactions although the main effect seems to be on de novo purine biosynthesis and CTP synthetase in mammalian cells (Lyons, S. D., Sant, M. E., Christopherson, R. I. (1990) *J. Biol. Chem.* 265, 11377–11381). It blocks proliferation and has gone through extensive clinical trials as a cancer drug (reviewed in Catane, R., Von Hoff, D. D., Glaubiger, D. L. and Muggia, F. M. (1979) *Cancer Treat. Rep.* 63, 1033–1038; and Ahluwalia, G. S., Grem, J. L., Hao, Z., and Cooney, D. A. (1990) *Pharmacol. Ther.* 46, 243–271). U.S. Pat. No. 2,965,634 relates to norleucine derivatives, such as DON, and a process for the production thereof. The use exemplified therein is based on the phytotoxic properties thereof, e.g. as herbicides or deweeding agents. There is nothing mentioned which would lead the skilled in this field to contemplate use of norleucine derivatives in medicaments. Thus, the present invention disclose for the first time the use of DON in the treatment of clinical conditions caused by protozoan pathogens. As shown below in the experimental section, already at 1 μM, DON completely blocked trypanosome proliferation and it selectively lowered the CTP level in *T. brucei* without affecting the UTP, ATP or GTP levels.

In an alternative embodiment, the CTP inhibitor is acivicin. Similar to DON, acivicin has been suggested for use as an active component in a herbicidal composition, see e.g. U.S. Pat. No. 5,489,562.

As mentioned above, in order to provide an efficient medicament for use in treatment schemes, toxic effects of the CTP synthetase inhibitor should be suppressed by use of a suitable nucleobase, such as a purine base or a nucleoside. As an illustration, in mammalian cells, DON is known to also affect the de novo purine biosynthesis, a pathway lacking in trypanosomes. According to the present invention, this is the main target of the drug in tissue cultured mouse fibroblasts. Without any purines in the culture medium, a total block of proliferation occurred at 1–2 μM. However, the addition of the purine base hypoxanthine is shown in the experimental section below to increase the DON concentration needed for a proliferation block to more than 20 μM. Cytidine had no such effect. Accordingly, the best embodiment of the present invention seems to be a combination therapy of DON and hypoxanthine.

In an advantageous embodiment, the purine base is selected from the group consisting of adenine, guanine, allopurinol and/or hypoxanthine. However, since nucleosides are split into sugar and purine base when administered, in an alternative embodiment, a nucleoside is used as the component suppressing the toxic side effects of the glutamine analogue used. Thus, the purine base is then provided by use of a nucleoside, e.g. adenosine, guanosine or inosine, in the present manufacture. The preparation of purines and nucleosides is well known to those of skill in this field and may follow any conventional method, see e.g. U.S. Pat. Nos. 6,017,736, 5,792,868 and 5,688,947.

The present use is preferably related to a medicament for the treatment and/or prevention of a disease selected from the group consisting of malaria, leishmaniasis and trypanosomiasis, e.g. American trypanosomiasis (Chaga's disease), or African trypanosomiasis (African sleeping sickness).

In a second aspect, the present invention relates to a pharmaceutical composition for the treatment and/or prevention of a disease caused by a parasitic protozoa, which comprises an inhibitor of CTP synthetase and a purine base together with a pharmaceutically acceptable carrier and optionally other excipients.

In all essential, the present pharmaceutical composition will be manufactured as described above. Thus, the inhibitor of CTP synthetase is a glutamine analogue, such as 6-diazo- 5-oxo-L-norleucine (DON) or acivicin, while the purine base has been selected from the group consisting of adenine, guanine and/or hypoxanthine. In a specific embodiment, the purine base is provided to the composition by use therein of a nucleoside, e.g. adenosine, guanosine and inosine, or any functional equivalent or derivative thereof capable of inhibiting toxic effects of a glutamine analogue.

The pharmaceutical composition according to the invention may be presented as one single composition, wherein the components are present in an admixture in said carrier. Alternatively, the composition is pesented in a kit form, wherein the components are present as separate entities for essentially simultaneous administration the the patient. The choice of form will be dependent on prevaining circumstances and practical reasons by the skilled in this field.

It is possible to administer the active ingredients according to the invention alone in solution. However, in the preferred embodiment, the active ingredient(s) are formulated into a pharmaceutical composition. The present composition comprises at least one active ingredient (CTP synthetase inhibitor, a nucleobase, such as a purine or nucleoside), together with one or more pharmaceutically acceptable carriers and/or other therapeutic agents. As included within the scope of this invention, "acceptable" is defined as being compatible with other ingredients of the formulation and non-injurious to the patient or host cell. These carriers include those well known to practitioners in the art as suitable for oral, rectal, nasal, topical, buccal, sublingual, vaginal, or parenteral (including subcutaenous, intramuscular, intravenous, and intradermal) administration, intervenous or oral administration being preferred. Specific carriers suitable for use in the invention are well known to those of skill in this field and may be as mentioned below.

The present composition may be administered orally in liquid or in tablet form, and may include one or more of the following: lactose (hydrous, fast flow), microcrystalline cellulose, colloidal silicon dioxide, croscarmellose sodium, magnesium stearate, stearic acid, and other excipients, colorants, and pharmacologically compatible carriers. Since the present composition is instable in acidic media, in order to enable release thereof in the intestine, the acidic environment in the stomach must be compensated for when oral doasage forms are used. Thus, the present composition may either be taken together with a suitable buffer, such as bicarbonate. Alternatively, it may be coated with an enteric coating. An isolation of the active ingredient from the acidity of the enteric coating may also be included, such as by use of an isolating layer. The preparation of enteric coatings is well known to the skilled in this art. Compositions for oral use may be administered to patients in fasting and non-fasting states.

If formulated for for parenteral administration, the present composition may include aqueous and non-aqueous, isotonic sterile injection solutions which may contain antioxidants, buffers, bacteriostats and solutes which render the active ingredient(s) isotonic with the blood of the intended recipient; and aqueous and non-aqueous sterile suspensions which may includes suspending agents and thickening agents. As discussed above, the composition may be presented in unit-dose or multi-dose sealed containers, for example, ampules and vials, and may be stored in a freeze-dried (lyophilized) condition requiring only the addition of the sterile liquid carrier, for example, water for injections, immediately prior to use. Extemporanenous injection solutions and suspensions may be prepared from sterile powders, granules and tablets of the kind previously described.

The doses will need to be modified according to the clinical condition to be treated as well as on the patient's age, body weight etc. Suitable doses are determined for each specific case by the medical practioner responsible.

The pharmaceutical composition according to the invention is formulated for use in the treatment and/or prevention of a disease selected from the group consisting of malaria, leishmaniasis and trypanosomiasis, e.g. American trypanosomiasis (Chaga's disease), or African trypanosomiasis (African sleeping sickness).

In a third aspect, the present invention relates to a method of treatment and/or prevention of a disease caused by a parasitic protozoa, which comprises the administration to a patient in need of therapy of a therapeutic amount of a composition as defined above. Thus, all details discussed above are also considered and possible embodiments of the present method of treatment.

In a last aspect, the present invention relates to a model system comprising recombinant *T. brucei*, wherein an inducible promoter has been inserted to control the CTP synthetase gene, for studies of lipids, membranes and marker proteins for various life cycle stages of *T. brucei*. Such studies are useful e.g. for future drug development, since it is not yet exactly known what mechanism triggers trypanosomes to go through the radical changes in morphology and metabolism when they switch between various life cycle stages. There is a great need to synthesize lipids during these changes. Trypanosomes have one large mitochondrion-like organelle called kinetoplast, which go through a dramatic increase in size and amount of cristae when the trypanosomes develop from blood stream forms to insect procyclic forms (Vickerman, 1985). Lipids are needed for this process as well as for the general reorganization of the plasma membrane that accompany the development of the parasites. In the present work, it is shown that the CTP level is very low as long as the trypanosomes are in the mammalian bloodstream (around 0.5% of the total NTP pool). However, in the procyclic form, which is the first developmental stage in the fly, the level is much higher (around 4% of the total NTP pool). Maybe the CTP synthesis is tuned up to accommodate to an increased demand of lipids. In many systems, CTP has been shown to play a key role in the regulation of lipid synthesis (Vance, D. E., Trip, E. M. and Paddon, H. M. (1980) *J. Biol. Chem.* 255, 1064–1069; and Lopez, G. C. and Wurtman, R. I. (1992) *J. Neurochem.* 59, 338–343).

The present inventors have previously shown (Hofer, A., Ekanem, J. T. and Thelander, L. (1998) *J. Biol. Chem.* 273, 34098–34104) that the low CTP and CDP pools did not lead to a low dCTP pool in the cultured blood stream form, implicating that ribonucleotide reductase could compensate for the low cytidine nucleotide pools. However, in the long slender forms isolated from mice also the dCTP pool is low. The CTP (and presumably CDP) pools seem to be below the level that ribonucleotide reductase can compensate for. It is less surprising that the dCTP pool is low in the short stumpy form since it is not proliferating.

Accordingly, there is a need to know how the parasites accomplish to increase their CTP level almost tenfold when transforming from bloodstream to insect forms. The present invention shows that the only way for trypanosomes, at least for the cultured bloodstream form, to make CTP is by de novo synthesis and that the regulation of the CTP pool is through synthesis rather than by degradation of CTP. All these evidences point towards CTP synthetase as the key player in the regulation of the CTP level. The present model system is provided to enable putting the CTP synthetase under an inducible promoter in *T. brucei* to observe what happens with lipids, membranes and marker proteins for various life cycle stages upon induction.

DETAILED DESCRIPTION OF THE DRAWINGS

FIG. 1 shows the NTP pools in *T. brucei* from different life cycle stages. In A) all the NTPs are shown, while in B), the region showing the CTP pools have been magnified. The CTP peak is made up of both CTP and dCTP. The part representing dCTP is indicated by black color. The samples are from procyclic (PC), long slender (LS), short stumpy (SS) and in vitro cultured blood stream forms (C). The abbreviation for each life cycle stage (PC, LS, SS, C) is put below the corresponding box in B) and the same order of the samples are used in A). All values are averages with standard deviations indicated by error bars except the C value that is an average of 19 experiments and the dCTP levels from long slender and short stumpy forms that are single measurements. The values are represented as relative (in %) to the total NTP pool (CTP+UTP+ATP+GTP). Thus, even though it appears that the UTP, ATP and GTP pools are similar in all forms of the parasite, the CTP pool (better seen in FIG. 1B) in the procylic form (PC) is much higher than the mammalian forms (LS, SS, C). The trypanosomes grown in mice (long slender, LS, and short stumpy, SS, forms) have even lower CTP pools than the cultured bloodstream forms (C).

Figure 2:
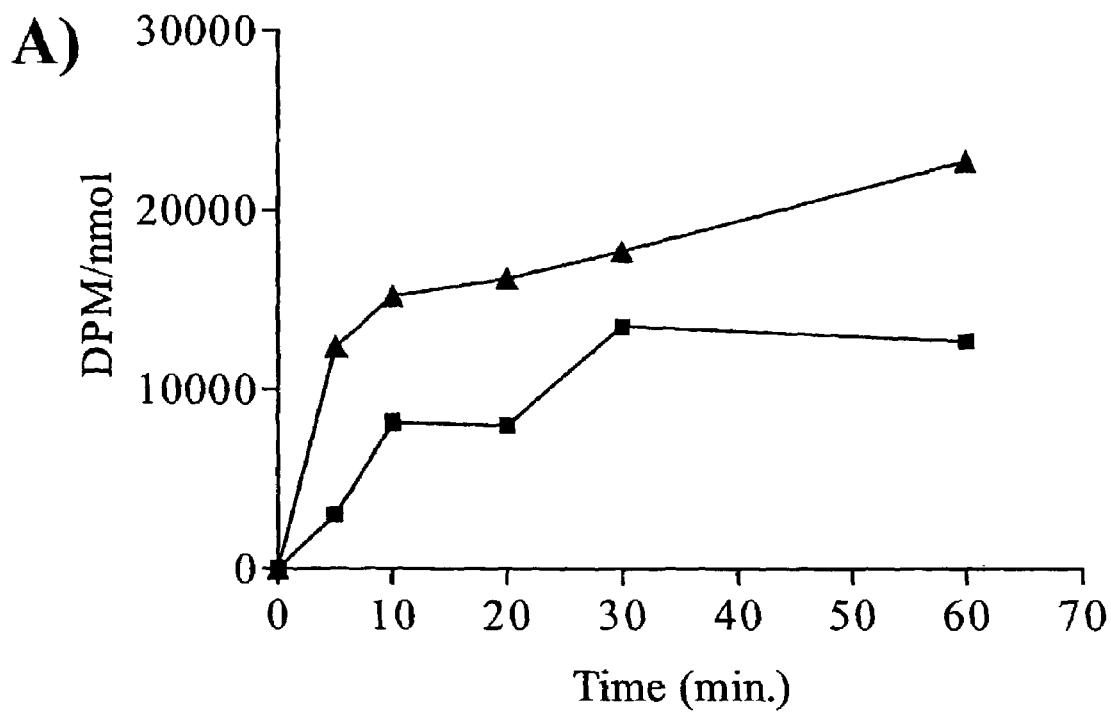
FIG. 2 shows the incorporation of tritium label into CTP, UTP and nucleic acids. In A), the incorporation of tritium into UTP (triangles) and CTP (squares) is shown, while in B), the incorporation of label into RNA+DNA (squares) and only DNA (triangles) is shown.
Figure 2:
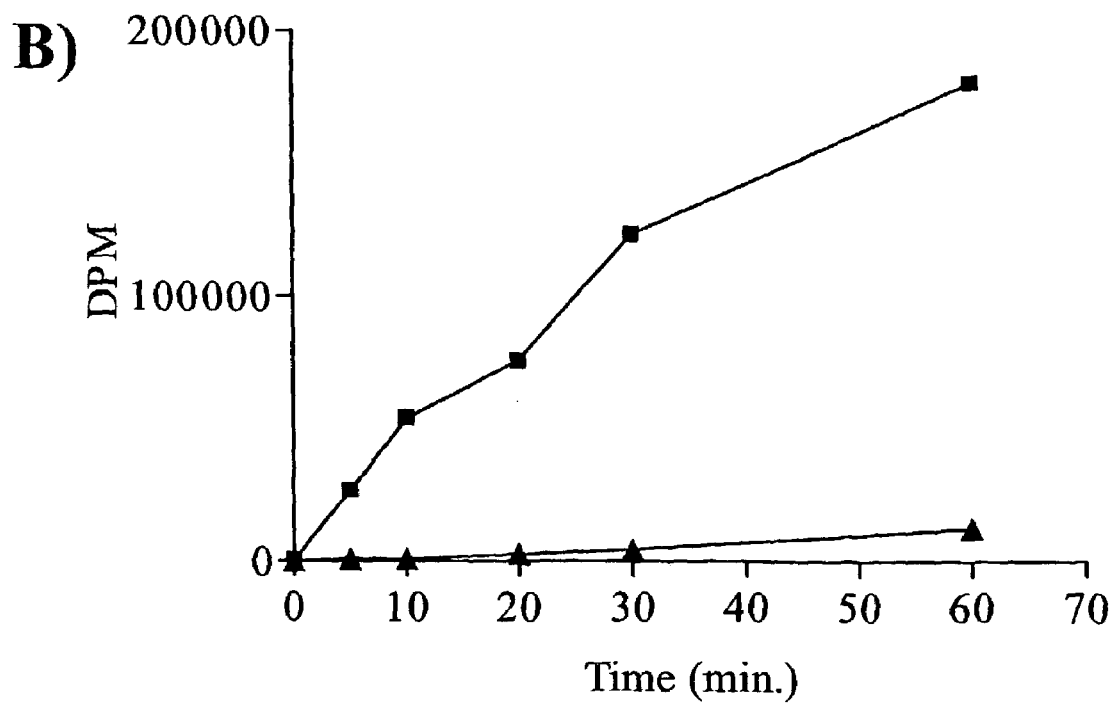

FIG. 2 shows the incorporation of tritium label into CTP, UTP and nucleic acids. 200 ml trypanosomes were collected by centrifugation and resuspended in 20 ml medium. After 30 min. preincubation at normal growth conditions they were given tritiated uracil and collected at various time points. In A), the incorporation of tritium into UTP (triangles) and CTP (squares) is shown. The values are plotted as specific activities (DPM/nmol of each nucleotide). It appears that tritium was not only incorporated into the UTP, but also the CTP pool. In B), the incorporation of label into RNA+DNA (squares) and only DNA (triangles) is shown. In this case, absolute values (DPM) are shown.

Figure 3:
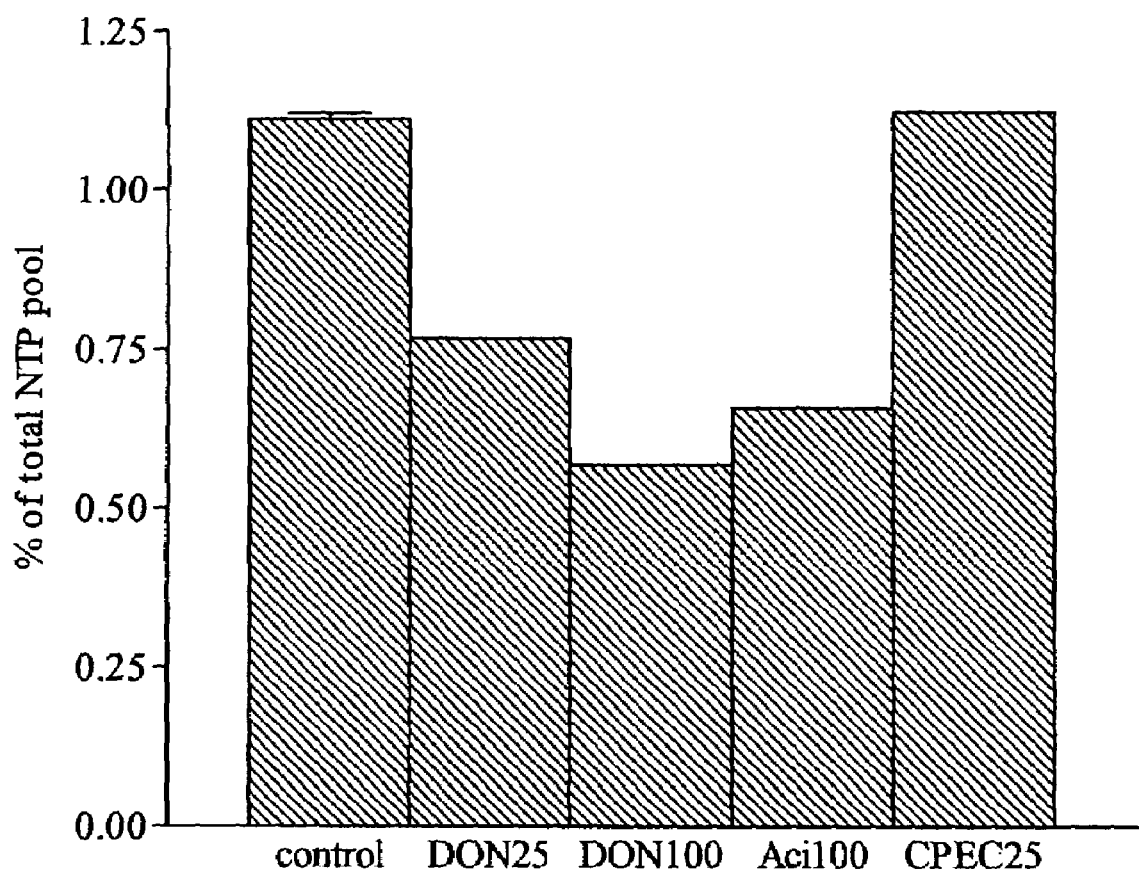
FIG. 3 shows the CTP pools after the treatment with various CTP synthetase inhibitors for 1 h. Samples are shown without drug (control), with 25 and 100 μM DON (DON25 and DON 100, respectively), with 100 μM acivicin (Aci100) and with 25 μM CPEC (CPEC25).

FIG. 3 shows the CTP pools after the treatment with various CTP synthetase inhibitors for 1 h. Samples without drug (control), with 25 and 100 μM DON (DON25 and DON100, respectively), with 100 μM acivicin (Aci100) and with 25 μM CPEC (CPEC25) are shown. The unit of the ordinata is the same as in FIG. 1. The control is an average of two experiments while the others are single measurements.

Figure 4:
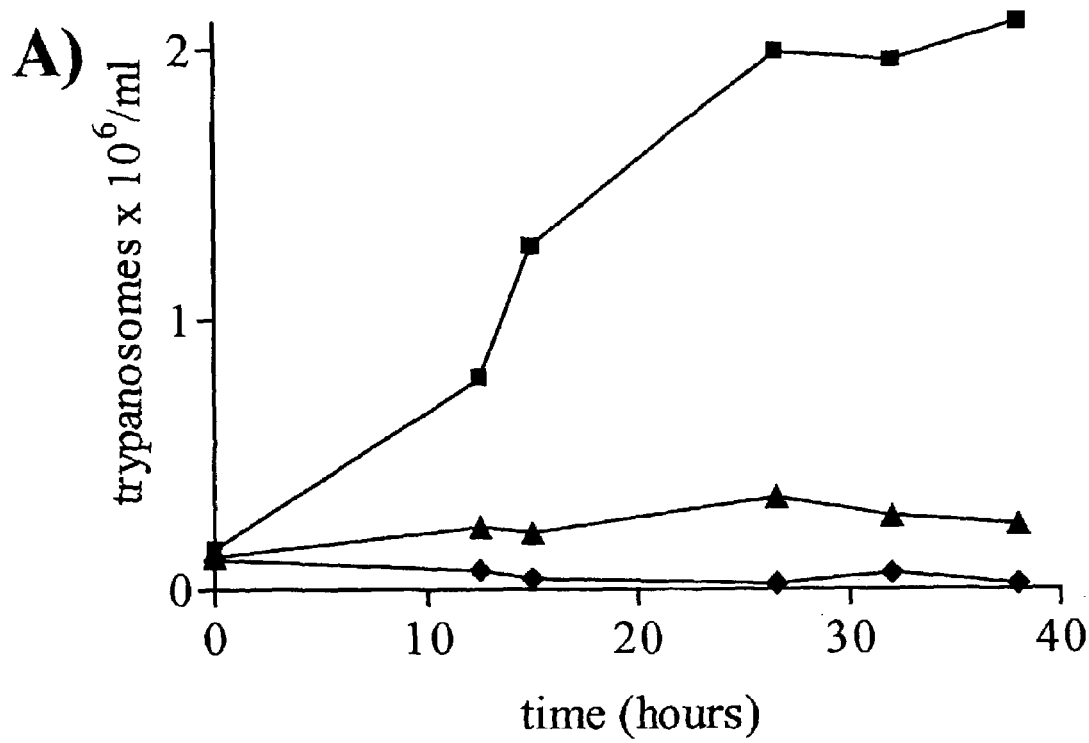
FIG. 4 shows the effect of DON (A) and acivicin (B) on trypanosome proliferation. In A), the trypanosomes were treated with no drug (squares), 1 μM DON (triangles) or 5 μM DON (diamonds). In B), the trypanosomes were treated with no drug (filled squares), 1 μM acivicin (triangles), 5 μM acivicin (diamonds) or 25 μM acivicin (open squares).
Figure 4:
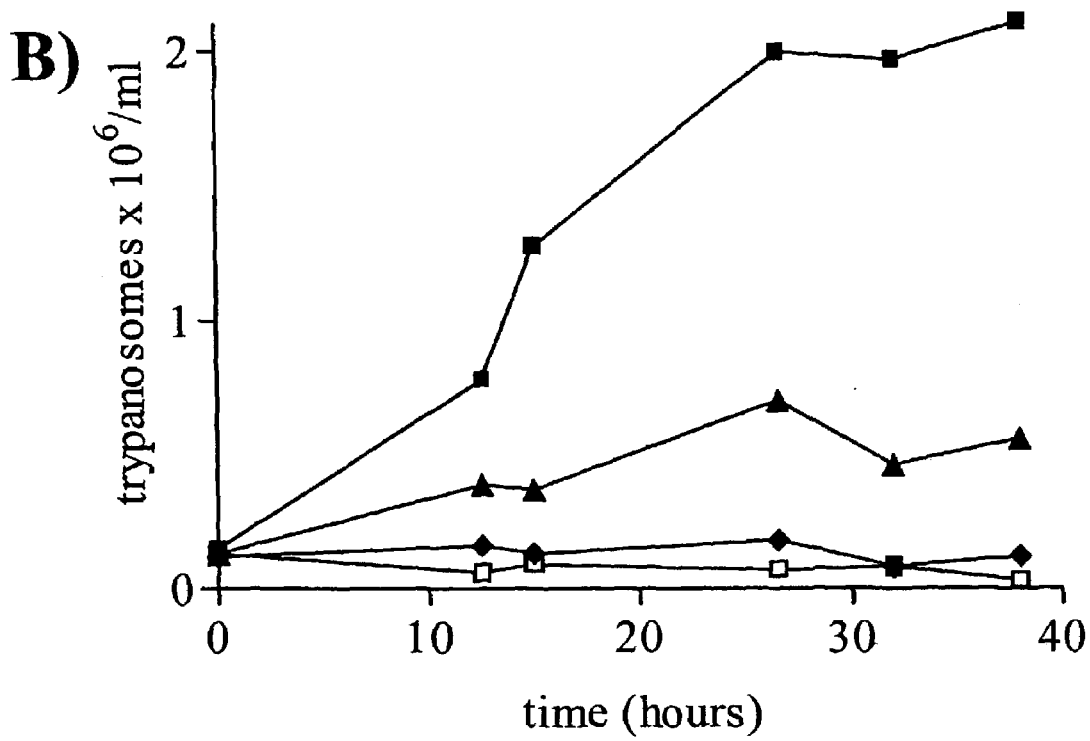

FIG. 4 shows the effect of DON (A) and acivicin (B) on trypanosome proliferation. In A), the trypanosomes were treated with no drug (squares), 1 μM DON (triangles) or 5 μM DON (diamonds). In (B), the trypanosomes were treated with no drug (filled squares), 1 μM acivicin (triangles), 5 μM acivicin (diamonds) or 25 μM acivicin (open squares). The number of trypanosomes was counted at various time-points after the drug exposure had started. It appears that DON and acivicin were both very active.

Figure 5:
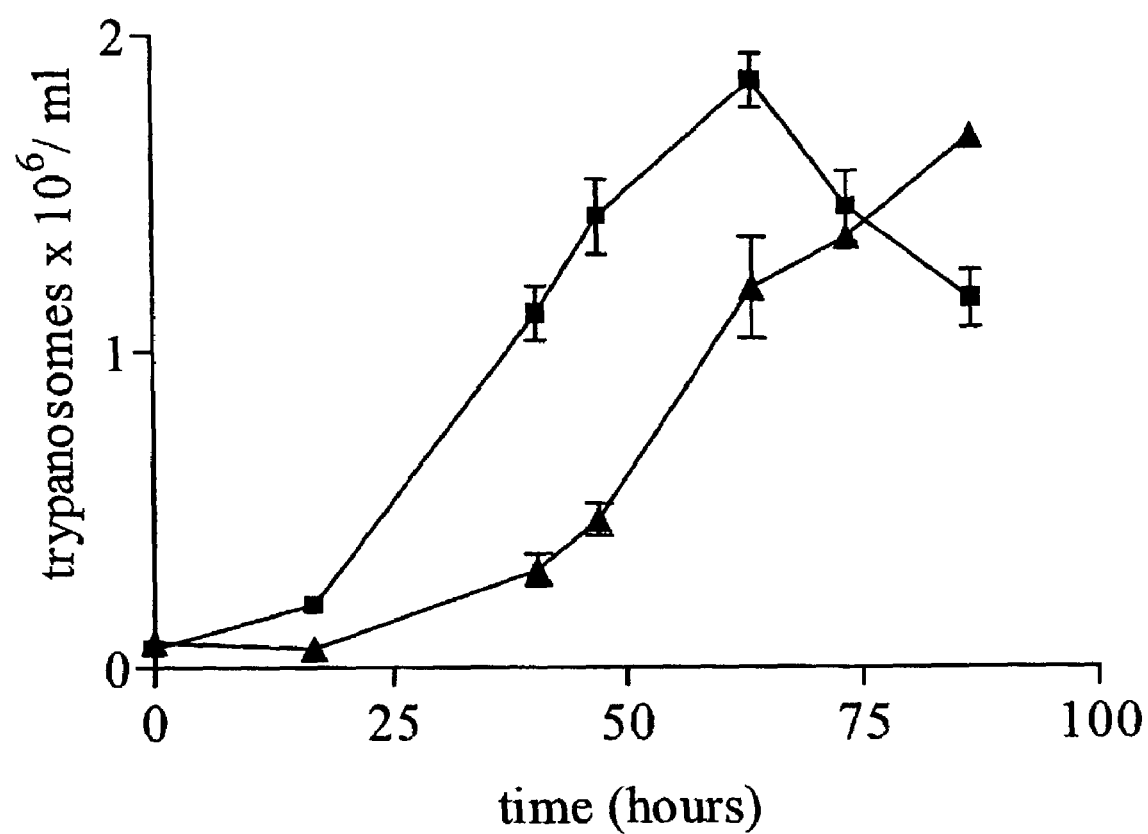
FIG. 5 shows the release after exposure to 5 μM DON for 1 h. The trypanosomes were treated with DON for 1 h and then harvested and resuspended in drug-free medium.

FIG. 5 shows release after exposure to 5 μM DON for 1 h. The trypanosomes were treated with DON for 1 h and then harvested and resuspended in drug-free medium. The number of trypanosomes was counted at various time-points after the release had started (triangles). A control experiment was performed where the trypanosomes were not exposed to DON but otherwise were treated exactly the same way as the drug-treated trypanosomes (squares). Each point is an average of two experiments with the standard deviation indicated by error bars.

Figure 6:
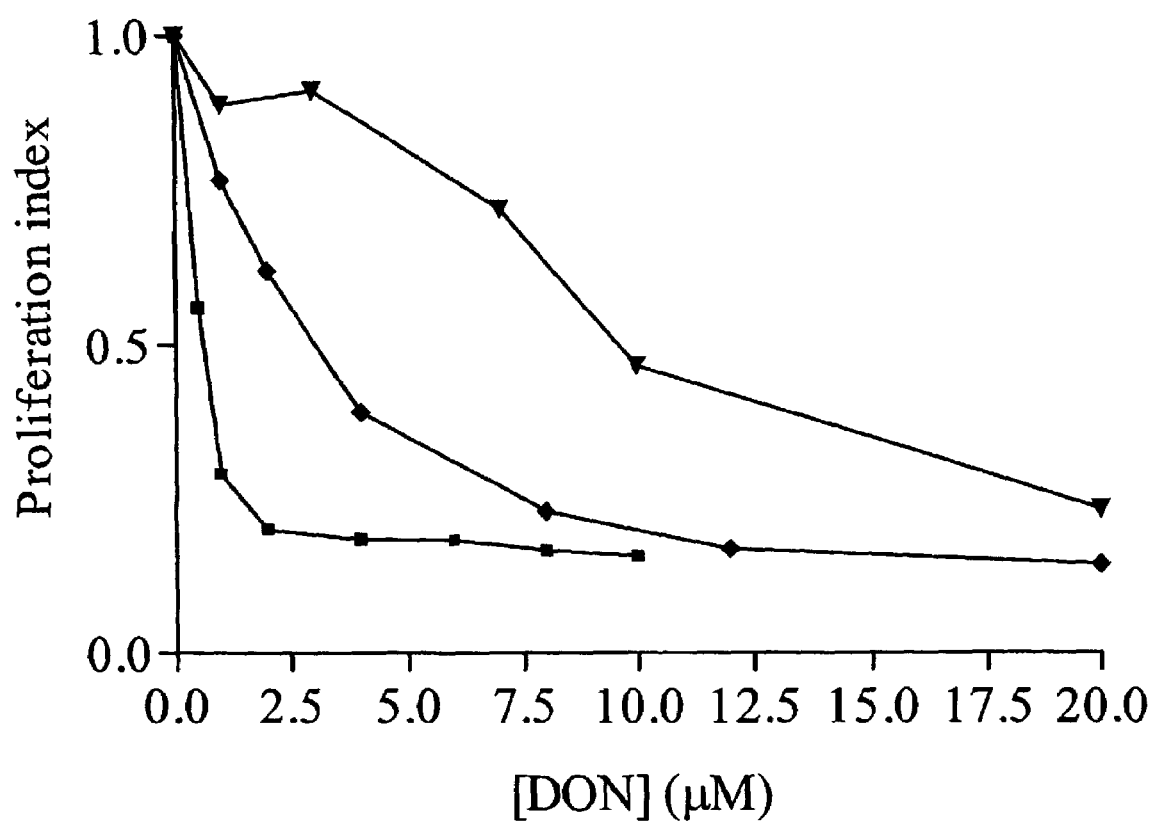
FIG. 6 shows the proliferation of mouse BALB/c fibroblasts with increasing DON concentrations in the absence (squares) or presence of 10 μM (diamonds) of 160 μM hypoxanthine (triangles). The proliferation index on the ordinata shows the relative amount of cells as compared to the sample without drug.

FIG. 6 shows proliferation of BALB/c fibroblasts with increasing DON concentrations in the absence (squares) or presence of 10 μM (diamonds) of 160 μM hypoxanthine (triangles). The fibroblasts were seeded at a density so low that they could not get confluent within three days. When they had settled on the plates, they were exposed to the drugs and left for three days. At this point the amount of cells was indirectly counted by a method described in the section "Material and methods" below. The proliferation index on the ordinata shows the relative amount of cells as compared to the sample without drug.

Experimental

Below, the present invention will be illustrated by way of examples, which are not intended to limit the invention as defined by the appended claims. All references given below and elsewhere in the present specification are hereby included herein by reference.

Material and Methods

Handling of Trypanosomes and Mammalian Cells

Bloodstream forms of the pleomorphic *T. brucei brucei* variant clone AnTat 1.1 (Van Meirvenne, N. Janssens, P. G. and Magnus, E. (1975) *Ann. Soc. Belge Med. Trop.* 55, 1–23) were grown in NMRI mice. Long slender trypanosomes were purified on day 3 post injection and short stumpy trypanosomes on day 5 post injection from blood by DEAE-cellulose chromatography (Lanham, S. M. and Godfrey, D. G. (1970) *Exp. Parasitol.* 28, 521–534). The trypanosomes were confirmed to be long slender forms (33–35% was in S-phase) and short stumpy forms (only 6–7% was in S-phase) by flow cytometry.

Procyclic insect forms of *T. brucei brucei* AnTat 1.1 were cultured in SDM-79 medium (Brun, R. and Schoenenberger, M. (1979) *Acta Trop.* 36, 289–292) supplemented with 10% heat-inactivated fetal bovine serum at 27° C. Culture-adapted bloodstream forms of the *T. brucei brucei* cell line TC221 (Hirumi, H., Hirumi, K., Doyle, J. J. and Cross, G. A. M. (1980) *Parasitology* 80, 371–382) were propagated in Hirumi's modified Iscove's medium-9 (Hirumi, H. and Hirumi, K. (1989) *J. Parasitology* 75, 985–989) supplemented with 5% fetal bovine serum at 37° C. in a humidified atmosphere containing 7% CO2. The cultured parasites were harvested in the late logarithmic growth phase.

Mouse Balb/c fibroblasts were cultivated as monolayers in Dulbecco's Modified Eagles Medium (Sigma) supplemented with L-glutamine (0.584 g/l) and 10% heat-inactivated horse serum at 37° C. in a humidified atmosphere containing 7% $CO_2$. The amount of fibroblasts on each plate was determined by a method were the cell-containing plates were washed with PBS pH 7.5, the cells disintegrated by a 10 min. incubation with 0.2 M NaOH at 50° C. and then the $OD_{260-310}$ was measured (Suttle, D. P. and Stark, G. R. (1979) *J. Biol. Chem.* 254, 4602–4607). The cells were collected before confluence.

Measuring of NTP Pools $1–3 \times 10^8$ trypanosomes were collected and subsequently disintegrated by 500 μl ice-cold 0,6 M trichloroacetic acid supplemented with 15 mM $MgCl_2$. The trichloroacetic acid was removed by two extractions with 720 μl 1,1,2-trichlorotrifluoroethan (78%)/trioctylamine (22%) and the aqueous phase was saved. ⅕ of the sample was evaporated to dryness in a Speedvac (Savant), loaded onto a 4.6×125 mm Partisphere SAX-column and run by HPLC in 0,5 M ammonium phosphate pH 3,4 containing 2,5% acetonitrile at 1.5 ml/min. The procedure is further explained in previous work by the present inventors, see Hofer, A., Ekanem, J. T. and Thelander, L. (1998) *J. Biol. Chem.* 273, 34098–34104. A connection of the HPLC to a Flow Scintillation Analyzer (Radiomatic 150 TR, Packard) made it possible to check the radioactivity in the chromatographic peaks. For radioactivity measurements, the whole sample was usually loaded onto the column. The nucleotides were quantified by measuring the peak heights and comparing them to a standard curve.

Deoxyribonucleotides were separated from ribonucleotides on a boronate column before they were analyzed by Partisphere SAX-chromatography.

Determination of Ribonucleoside and Nucleobase Content in the Culture Medium

The sample (200 µl culture medium) was centrifuged through a Nanosep 3K filter (Pall Filtron Corporation) and various amounts of sample were loaded onto a 4.6×150 mm Discovery HPLC column (Supelco) and run by HPLC in 10 mM ammonium phosphate pH 3.4 at 1 ml /min. The peaks were identified by their A260/A280 and from the retention times of standard nucleosides and bases mixed with culture medium. The ribonucleosides and bases were quantified by measuring the peak heights and comparing them to a standard curve.

Conversion of Tritiated Uracil into UTP, CTP, Cytidine, Uridine, RNA and DNA 200 ml trypanosomes in logarithmic growth phase (~0.5–1×106 trypanosomes/ml) were collected by centrifugation (2 min. at 3000 RPM) and resuspended in 20 ml cultivation medium. After 30 min. preincubation at 37° C. and 7% $CO_2$, they were given a final concentration of 0.13 µM 39 Ci/mmol [5,6-3H]-uracil (Moravek Biochemicals Inc.) and incubated for various amounts of time. A similar experiment was also tried with a final concentration of 0.34 µM 14.7 Ci/mmol [6-3H]-cytosine or 0.22 µM 22.9 Ci/mmol [5–3H(N)]-cytidin Radioactivity in the UTP, CTP, cytidine and uridine pools was determined by HPLC coupled to a Flow Scintillation Analyzer (see above). The material precipitated by TCA was dissolved in 0.6 M NaOH and incubated at 37° C. over night. Scintillation counting of this material revealed the total amount of radioactivity in nucleic acids (RNA+DNA). The amount of radioactivity in DNA could be recovered by TCA precipitation and collection on glass filters as described preciously (Nicander, B. and Reichard, P. (1985) *J. Biol. Chem.* 260, 5376–5381).

Drug Testing 6-diazo-5-oxo-L-norleucine (DON), acivicin and azaserine were bought from Sigma. They were dissolved in water and stored as 5 mM solutions at −20° C. Cyclopentenyl cytosine was a kind gift from Grant McClarty at the Dept. of Medical Microbiology, University of Manitoba, 730 William Ave, Winnipeg, Manitoba R3E OW3, Canada. It was stored as a 50 mM solution in dimethyl sulfoxide (DMSO) at 4° C. The final concentration of DMSO in the growth media of the trypanosomes never became more than 0.5% and that had no effect on the NTP pools or the proliferation of the parasites.

Results

Determination of NTP Pools in Various Stages of the *T. brucei* Life Cycle

It was desired to check if the low CTP level previously reported by the present inventors for cultured bloodstream forms (Hofer, A., Ekanem, J. T. and Thelander, L. (1998) *J. Biol, Chem.* 273, 34098–34104) also holds in vivo.

Therefore, the NTP pools in long slender and short stumpy trypanosomes grown in mice were checked. The procyclic form, which is one of the stages in the tsetse fly, was also included to see if the concentration of CTP is low in all life cycle stages or if it possibly is involved in the switch between life cycle stages. As seen in FIG. 1A, the UTP, ATP and GTP pools are similar in all forms of the parasite. However, the CTP pool (better seen in FIG. 1B) in the procylic form (PC) is much higher than the mammalian forms (LS, SS, C). The trypanosomes grown in mice (long slender, LS, and short stumpy, SS, forms) have even lower CTP pools than the cultured bloodstream forms (C). The dCTP pool was also checked and it was noticed that it was about similar in the insect form and the cultured bloodstream form while the two forms purified from mice also had low dCTP pools.

The Turnover of the CTP Pool

It was desired to investigate why the CTP pool is so low in the trypanosomes. This could either be by deficient synthesis or excessive degradation of CTP. In other systems CTP can either be synthesized de novo from UTP or from salvage of cytidine. In a few organisms, such as *Giardia lamblia*, cytosine can also be salvaged (Aldritt, S. M., Tien, P. and Wang, S. S. (1985) *J. Exp. Med.* 161, 437–445). When the trypanosomes were given up to 15 mM cytidine or 1 mM cytosine and harvested one hour later, no change in the size of the CTP pool could be detected. Likewise, if the trypanosomes were given tritiated cytidine or cytosine, no label could be detected in the CTP pool. It was confirmed by HPLC chromatography that the added cytidine was not degraded to uridine by cytidine deaminase in the serum during the incubation. Thus, there seems to be no salvage of cytidine or cytosine in *T. brucei*. The de novo pathway was then tested. Trypanosomes were given tritiated uracil and harvested at various incubation times. Tritium was not only incorporated into the UTP but also the CTP pool (FIG. 2A). Thus, it was concluded that the trypanosomes have a de novo pathway for CTP synthesis. The accumulation of label in the UTP pool was rapid and almost saturated at 5 min, while the CTP pool was labeled at a much slower rate. This indicated that a slow de novo synthesis could be responsible for the low CTP level. It was also desired to investigate if the size of the CTP pool was controlled by a high degradation rate of CTP. Therefore, the label in two degradation products of CTP catabolism, cytidine and uridine, was checked by HPLC chromatography. No radioactivity at all could be detected in these peaks. On the contrary, label was readily incorporated into nucleic acids (FIG. 2B). Considering the detection limit of labeled cytidine and uridine in the present analysis, it can be concluded that at least 95% of the CTP in the trypanosomes is used for RNA and DNA synthesis. A rapid degradation is thus not responsible for the low CTP pool in *T. brucei*.

Testing of CTP Synthetase Inhibitors

The absolute dependence on de novo synthesis for CTP production might be exploited for chemotherapy purposes since the host can be rescued by cytidine. There are two major classes of compounds that inhibit CTP synthetase, nucleoside analogues and glutamine analogues. One nucleoside analogue, cyclopentenyl cytosine (CPEC), and two glutamine analogues, 6-diazo-5-oxo-L-norleucin (DON) and acivicin, were tested and it was observed how the CTP pool changed during the one-hour incubation period (FIG. 3). CPEC had no effect while DON and acivicin both lowered the CTP pool. Acivicin was less specific than DON since also the GTP pool was reduced by 50% (not shown in the figure). Next, the effect of the drugs on trypanosome growth was investigated. DON and acivicin were both very active (FIGS. 4A and B, respectively), especially DON that completely blocked proliferation already at a concentration of 1 μM. As expected. CPEC (250 μM) had no effect in this experiment either (data not shown). Cytidine (up to 5 mM) or cytosine (1 mM) could not rescue the trypanosomes from the proliferation block asserted by DON, a logical result since it has already been shown that *T. brucei* cannot salvage cytidine or cytosine.

DON is not stable in the bloodstream and has a half-life of only a few hours in humans (Kovach, J. S., Eagan, R. T., Pawis, G., Rubin, J., Creagan, E. T. and Moertel. C. G. (1981) *Cancer Treat. Rep.* 65, 1031–1036; Rahman, A., Luc, V., Smith, F. P., Vrown, J., Schein, P. S. and Woolley, P. V. (1981); and Sullivan, M. P., Nelson, J. A., Feldman, S. and Nguyen, B. V. (1988) *Cancer Chemother. Pharmac.* 21, 78–84). Therefore, it was tested for how long the effect of a short pulse of DON lasts on trypanosome proliferation. In FIG. 5, the trypanosomes have been treated with 5 μM DON for 1 h. After the incubation, the trypanosomes were collected by centrifugation, the pellet was washed with media not containing DON and resuspended in the same media and the trypanosomes were put back into the incubator. The amount of trypanosomes was continuously recorded during the incubation. Control trypanosomes were treated the same way except that the one-hour incubation was without DON. As seen from the figure the effect of the 1 h-incubation with DON stayed on for approximately 20 h before the trypanosomes started to proliferate again.

Combination of DON and Hypoxanthine

The effect of DON on trypanosomes and mammalian cells was compared as follows. In FIG. 6, it is shown that DON has a profound effect on proliferation of cells since already at 1–2 μM maximal inhibition occurs. At this point the amount of cells after 72 h is about the same as before the incubation with DON started (data not shown). No proliferation has thus occurred during the three incubation days. An even higher DON concentration does not lower the amount of cells further. However, the remaining cells look very strange in morphology and are obviously sick. Thus, it needed to be investigated whether or not the anti-proliferation effect on mammalian cells could be abolished, while still keeping the trypanocidal activity. In mammalian cells, DON is a powerful inhibitor of de novo purine biosynthesis. In FIG. 6, two experiments are included wherein the block on de novo purine biosynthesis have been by-passed by 10 and 160 μM hypoxanthine, respectively. Hypoxanthine is a naturally occurring purine base in the bloodstream of mammals. In the presence of 160 μM hypoxanthine, the DON concentration needed to inhibit proliferation was around 20 times higher than without hypoxanthine. With 10 μM hypoxanthine, the antiproliferative effect of DON was still high and when the medium was checked after the incubation it was found that the hypoxanthine was consumed during the experiment. This means that 10 μM hypoxanthine probably has an even higher effect than indicated in the figure. Trypanosomes, which do not have any de novo synthesis of purines, are grown in the presence of 160 μM hypoxanthine in all the present experiments.

EXAMPLE 1

Effect of 6-diazo-5-oxo-L-norleucine (DON)

In order to determine in what range DON is effective against *Plasmodium falciparum*, the cause of malaria, Swiss Tropical Institute (Socinstrasse 57, P.O. Box, CH, 4002 Basel, Switzerland) performed the present experiment according to their standard methods available as a commercial service provided under secrecy (for an exact disclosure of the method, reference is made to Swiss Tropical Institute). Further, the present experiment enables a comparison between the effect of DON on both *Trypanosoma brucei rhodiense* and *Plasmodium falciparum*.

The results were as shown in Table 1 below.

TABLE 1

| Parasite | IC50 (μM) |
| --- | --- |
| *Trypanosoma brucei rhodiense* | 0.43 |
| *Plasmodium falciparum:* | |
| -KI isolate | 0.52 |
| -NF54 isolate | 0.36 |

As appears from Table 1, the effect of DON for the treatment of malaria is in the same advantageous range as that for the treatment of African sleeping disease.

Discussion

The absolute dependence on the de novo pathway for CTP synthesis in *T. brucei* is promising for drug development. CTP synthetase inhibitors could be used together with cytidine that would only rescue the host since it is not converted to CTP by the trypanosomes. The most specific CTP synthetase inhibitor known is cyclopentenyl cytosine (CPEC). Unfortunately, CPEC did not inhibit CTP synthesis in *T. brucei*. CPEC and other pyrimidine nucleoside analogues are not likely to be metabolized to the active triphosphate form in *T. brucei* since it lacks uridine (Hammond, D. J. and Gutteridge, W. E. (1982) *Biochim. Biophys. Acta* 718, 1–10) and cytidine kinase activities. Mammalian cells have a cytidine-uridine kinase that, except for cytidine and uridine, phosphorylates a wide range of pyrimidine nucleoside analogues (Cihak, A. and Rada, B. (1976) *Neoplasma* 23, 233–257).

CTP synthetase catalyzes the transfer of an amino group from glutamine to UTP. Some glutamine analogues, such as 6-diazo-5-oxo-L-norleucine (DON), acivicin and azaserine, form covalent bonds with all kinds of glutamine aminotransferases. Among these are the proteins involved in de novo purine biosynthesis (two steps in the pathway leading up to IMP and the GMP synthase), de novo pyrimidine biosynthesis (carbamoyl phosphate synthetase II and CTP synthetase), NAD biosynthesis, glycosamine biosynthesis and the γ-glutamyl cycle (for a review see Ahluwalia, G. S., Grem, J. L., Hao, Z., and Cooney, D. A. (1990) *Pharmacol. Ther.* 46, 243–271). There are however large differences in specificity between various glutamine analogues for the various aminotransferases and DON primarily inhibits CTP synthetase and de novo purine biosynthesis (up to IMP) while acivicin inhibits CTP synthetase and GMP synthase and azaserine inhibits de novo purine (IMP) biosynthesis in mammalian cells (Lyons, S. D., Sant, M. E., Christopherson, R. I. (1990) *J. Biol. Chem.* 265, 11377–11381). The specificity of these analogues seems similar in the trypanosomes to the mammalian cells with the exception that trypanosomes lack de novo purine biosynthesis and therefore are insensitive to drugs affecting this pathway. Azaserine had no effect on trypanosome proliferation (data not shown) and DON did not alter the purine NTP pools in the trypanosomes.

Many facts look promising for the use of DON against sleeping sickness. The present inventors have discovered that the growth inhibiting effect of a 1 h-DON exposure lingers on for 20 h before the trypanosomes start to proliferate again. This is a great advantage since clinical trials have shown that DON has a half-life of only a few hours in the human bloodstream (Kovach, J. S., Eagan, R. T., Pawis, G., Rubin, J., Creagan, E. T. and Moertel, C. G. (1981) *Cancer Treat. Rep.* 65, 1031–1036; Rahman, A., Luc, V., Smith, F. P., Vrown, J., Schein, P. S. and Woolley, P. V. (1981); and Sullivan, M. P., Nelson, J. A., Feldman, S. and Nguyen, B. V. (1988) *Cancer Chemother. Pharmac.* 21, 78–84). Furthermore, the present inventors could relieve the proliferation block on mammalian cells with hypoxanthine. Hopefully, a combination therapy of DON and hypoxanthine may relieve some of the side effects associated with DON. Since hypoxanthine is naturally occurring in the bloodstream, no severe toxic effects from this compound are expected. Hypoxanthine is known to cross the blood-brain barrier (Cornford, E. M. and Oldendorf, W. H. (1975) *Biochim. Biophys. Acta* 394, 211–219; and Spector, R. (1987) *Neurochem. Res.* 12, 791–796).

The invention claimed is:

1. A method of treatment of a disease caused by a parasitic protozoa, which comprises administering to a patient in need of such therapy a therapeutic amount of a pharmaceutical composition comprising
   a glutamine analogue that inhibits CTP synthetase, and
   a naturally occurring purine base, nucleoside or cytidine that suppresses toxic effects of the glutamine analogue in vivo
   together with a pharmaceutically acceptable carrier and optionally other excipients.

2. A method for the treatment of a disease caused by a parasitic protozoa comprising administering to a patient in need thereof
   a glutamine analogue that inhibits CTP synthetase, and
   a naturally occurring purine base, nucleoside or cytidine that suppresses toxic effects of the glutamine analogue in vivo.

3. The method according to claim 2, wherein said substance capable of suppressing toxic effects is a nucleoside.

4. The method according to claim 3, wherein the substance capable of suppressing toxic effects is a purine base.

5. The method according to claim 4, wherein the purine base is selected from the group consisting of adenine, guanine, hypoxanthine and mixtures thereof.

6. The method according to claim 4, wherein the nucleoside is selected from the group consisting of adenosine, guanosine, inosine and mixtures thereof.

7. The method according to claim 2, wherein the glutamine analogue is 6-diazo-5-oxo-L-norleucine (DON).

8. The method according to claim 2, wherein the glutamine analogue is acivicin.

9. The method according to claim 2, wherein the disease is selected from the group consisting of malaria, leishmaniasis and trypanosomiasis.

10. The method according to claim 9, wherein the trypanosomiasis is selected from the group consisting of American trypanosomiasis (Chaga's disease) and African trypanosomiasis (African sleeping sickness).

* * * * *